US012778634B2

(12) United States Patent
Theodoz et al.

(10) Patent No.: US 12,778,634 B2
(45) Date of Patent: Nov. 3, 2026

(54) REPOSITION AND PENETRATION FORCEPS AND EXTERNAL FIXATOR FOR FRACTURES OF LONG BONES

(71) Applicant: Technická univerzita v Kosiciach, Kosice-Sever (SK)

(72) Inventors: Molcányi Theodoz, Kosice (SK); Schnitzer Marek, Rozhanovce (SK); Hudák Radovan, Kosice (SK); Zivcák Jozef, Presov (SK)

(73) Assignee: TECHNICKA UNIVERZITA V KOSICIACH, Kosice-Sever (SK)

( * ) Notice: Subject to any disclaimer, the term of this patent is extended or adjusted under 35 U.S.C. 154(b) by 17 days.

(21) Appl. No.: 19/003,027

(22) Filed: Dec. 27, 2024

(65) Prior Publication Data

US 2026/0114904 A1 Apr. 30, 2026

(30) Foreign Application Priority Data

Dec. 29, 2023 (EP) .................................... 23220778

(51) Int. Cl.

| | |
|---|---|
| ***A61B 17/64*** | (2006.01) |
| ***A61B 17/60*** | (2006.01) |
| ***B33Y 80/00*** | (2015.01) |
| *A61B 17/29* | (2006.01) |

(52) U.S. Cl.

CPC .......... *A61B 17/6458* (2013.01); *B33Y 80/00* (2014.12); *A61B 2017/2926* (2013.01); *A61B 2017/2946* (2013.01); *A61B 2017/603* (2013.01)

(58) Field of Classification Search

CPC ..... A61B 17/62; A61B 17/64; A61B 17/6416; A61B 17/6458; A61B 2017/603

See application file for complete search history.

(56) References Cited

U.S. PATENT DOCUMENTS

| | | | |
|---|---|---|---|
| 4,502,473 | A | 3/1985 | Harris et al. |
| 4,570,625 | A | 2/1986 | Harris et al. |
| 5,769,851 | A | 6/1998 | Veith |

(Continued)

FOREIGN PATENT DOCUMENTS

| | | | | |
|---|---|---|---|---|
| CN | 101816583 | A | * | 9/2010 |
| CN | 205586068 | U | * | 9/2016 |

(Continued)

OTHER PUBLICATIONS

European Search Report dated May 29, 2024 for related European Patent Application No. EP23220778, 2 pages.

(Continued)

*Primary Examiner* — Jacqueline T Johanas
(74) *Attorney, Agent, or Firm* — Hovey Williams LLP; Paul J. Walker

(57) ABSTRACT

Reposition and penetration forceps for fractures of long bones, in particular traumatic fractures of tibia in centre line, that comprise two jaws forming a three-point system in opposition, wherein the first movable jaw (1) comprises two threaded pins (7) with tips (21) and the second firm jaw (2) comprises one threaded pin (7) with a tip (21). An external fixator for fractures of long bones, in particular traumatic fractures of tibia in centre line, which comprises at least two sets of forceps, wherein the sets of forceps are arranged identically or in a mirror image to each other.

14 Claims, 5 Drawing Sheets

(56) References Cited

U.S. PATENT DOCUMENTS

| | | | | |
|---|---|---|---|---|
| 6,537,275 | B2 | 3/2003 | Venturini et al. | |
| 6,840,939 | B2 | 1/2005 | Venturini et al. | |
| 7,147,639 | B2 | 12/2006 | Berki et al. | |
| 7,147,640 | B2 | 12/2006 | Huebner et al. | |
| 9,757,193 | B2 | 9/2017 | Zarins et al. | |
| 10,076,360 | B2 | 9/2018 | Tepic | |
| 2003/0153910 | A1 | 8/2003 | Janowski et al. | |
| 2005/0043730 | A1* | 2/2005 | Janowski | A61B 17/645 606/56 |
| 2006/0129163 | A1 | 6/2006 | Mcguire | |
| 2011/0208187 | A1* | 8/2011 | Wong | A61B 17/6416 606/56 |
| 2013/0110110 | A1 | 5/2013 | Waisman | |
| 2014/0276823 | A1* | 9/2014 | Schuele | A61B 17/6458 606/59 |
| 2018/0008315 | A1* | 1/2018 | Currier | A61B 17/6408 |
| 2018/0132897 | A1* | 5/2018 | Shiner | A61B 17/645 |
| 2020/0397480 | A1* | 12/2020 | Lavoritano | A61B 17/6416 |
| 2022/0022889 | A1* | 1/2022 | Hirt | A61B 17/645 |
| 2022/0346983 | A1* | 11/2022 | Arnette | A61F 2/78 |

FOREIGN PATENT DOCUMENTS

| | | | | | |
|---|---|---|---|---|---|
| CN | 108720911 | A | * | 11/2018 | A61B 17/6458 |
| CN | 210354870 | U | | 4/2020 | |
| CN | 210784618 | U | | 6/2020 | |
| CN | 112370131 | A | | 2/2021 | |
| CN | 212913351 | U | | 4/2021 | |
| CN | 107638205 | B | * | 8/2024 | |
| EP | 4578410 | A1 | * | 7/2025 | A61B 17/64 |
| ES | 2226791 | T3 | | 4/2005 | |
| FR | 2632851 | A1 | * | 12/1989 | A61B 17/6458 |
| JP | 11290338 | A | * | 10/1999 | |
| RS | P-2020/0867 | A1 | | 1/2022 | |
| SK | 2397 | U | | 2/2000 | |
| WO | WO-9730650 | A1 | * | 8/1997 | A61B 17/62 |
| WO | WO-2021191046 | A1 | * | 9/2021 | A61B 17/66 |

OTHER PUBLICATIONS

Peter R. Calder et al., The role of external fixation in paediatric limb lengthening and deformity correction, Injury, Int. J. Care Injured 50S (2019) S18-S23.

Giovanni De Bastiani et al., The Treatment of Fractures with a Dynamic Axial Fixator, Institute of Clinical Orthopaedics and Traumatology, University of Verona, The Journal of Bone and Joint Surgery, 1984, vol. 66-B, No. 4, Aug. 1985, 538-545.

G. De Bastiani et al., A rational alternative for the external fixation of fractures, International Orthopaedics (SICOT) (1986) 10: 95-99.

Levent Eralp et al., Distal Tibial Reconstruction with Use of a Circular External Fixator and an Intramedullary Nail, JPJS vol. 89-A, pp. 2218-2224, Oct. 2007, Istanbul, Turkey.

Proximal Tibia External Fixator—Orthopedic Drills, OrthopedicDrills.com, https://www.orthopedicdrills.com/product/proximal-Tibia-external-fixator/?doing_wp_cron=16636 . . . , 1z4, Jun. 26, 2025, 4 pages.

* cited by examiner

REPOSITION AND PENETRATION FORCEPS AND EXTERNAL FIXATOR FOR FRACTURES OF LONG BONES

RELATED APPLICATIONS

This application claims the priority benefit of European Patent Application Serial No. EP23220778.7 entitled "Reposition and Penetration Forceps and External Fixator for Fractures of Long Bones," filed Dec. 29, 2023, the entire disclosure of which is incorporated herein by reference.

TECHNICAL FIELD

The invention relates to reposition and penetration forceps and an osteosynthetic apparatus, an external fixator for fractures of long bones, comprising the reposition and penetration forceps.

BACKGROUND ART

External fixation is the gold standard for initiating stabilization of multiple fractures in severe polytrauma due to minimal invasiveness, and thus fitting without additional soft tissue damage and bone vascularization that are not caused as a result of an injury. Other advantages include the possibility of reposition directly with the fixator, faster application in emergency situations, achieving stability of a large number of bone fragments, reduced bleeding and the associated possibility of use for haemodynamically unstable patients.

External fixators are devices placed from the outside of the skin that stabilize bone fragments using basic structural components such as pins, wires, or they can also stabilise the fracture pinlessly, which is the least invasive method in which the medullary canal is not affected and thus can be referred to as nonmedullary.

If the fixator is equipped with pins or wires, there is a large variety of types of these osteosynthesis apparatuses such as Steinmann pins for bilateral frames, Schanz screws (self-drilling/pre-drilling required), Schanz screws with a small tip diameter used for small bones, Kirschner wires (1.8 mm and 2.0 mm) for circular fixators, and threaded K-wires for small external fixators. If the wires are used, they need to be stretched, which requires a circular construction.

Pins, wires and also pinless systems are mostly connected to one or more longitudinal rods or tubes of stainless steel or carbon fibre rods, and the whole construction is fixed with various types of clamps.

The standard tubular system is mainly used for the treatment of fractures of long bones, for arthrodesis, for bone lengthening and for transport systems. Due to the modular concept of the external fixator, it can be used in different variants of construction and configuration, which ensures enormous versatility.

An important parameter is the stiffness of the frame, which depends on:

- distance of the pins from the fracture line: the closer, the better;
- distance inside the fragment: the greater the lateral distance, the better;
- distance of the longitudinal tubes/rods from the bone: the closer, the better;
- number of rods/tubes: two are better than one;
- configurations (see FIG. 1): unilateral, V-shaped, bilateral or triangular frame.

Insufficiently stable external fixation can prolong fracture healing and lead to pin loosening. However, excessive stiffness or rigidity of the external fixator construction can also prolong fracture healing.

We currently have several types of external fixators:

- pin fixators (unilateral, V-shaped, bilateral, triangular),
- circular (wire) fixators,
- hybrid fixators (wire+pin),
- pinless external fixators.

The pin fixators are applied through the compacta, via the medullary canal to the opposing compacta. The surgical technique of inserting the pins must prevent penetration or damage to nerves, blood vessels and muscles, and the surgeon must use the proper placement of the pins in the so-called safe zones. Overall, this method is very stable, but on the other hand its fitting is not very easy and it involves penetration of the medullary canal with a high risk of infection and weakening of bone function.

The hybrid external fixator is a construct used for fractures close to the joint. It combines wire fixation (¾ of circular fixator) with pin fixation (unilateral fixator) in the diaphysis. It requires Kirschner wires for the ring and conventional Schanz screws for the rods. The Kirschner wires have an olive (olive-shaped thickening) that allows adaptation of the fragment by applying compression. Hybrid external fixators are less invasive than pin fixators due to the wires, thin wires are better anchored in porous bone than conventional pins, and they allow free movement in the joint after surgery. However, there are possibilities of joint infection, in addition, the close proximity of the Kirschner wire to the joint can be risky, and the radiation-impermeable ring may prevent evaluation with an X-ray image.

The main aim of the pinless fixators is to prevent penetration of the medullary canal and thus reduce the risk of deep infection. The sharp points of the fixator resemble a clip that is applied to the bone in a rolling motion and they should only penetrate the bone compacta. The clips of different sizes and shapes adapt to the triangular shape of the tibia at different levels. When the clips are properly anchored in the bone, they are connected through the rod by means of rod/rod clamps. This type of fixators is the least invasive, does not penetrate into the medullary canal and its fitting is simple and quick. However, they have a stability problem.

The frame construction of existing external fixators is based on local need and what is easiest. The fixator can be applied after the reposition (reposition first) or the fixator is used as a reposition tool (fixator first), in which case a modular frame construction is required.

The application of an external fixator as a reposition tool reduces the exposure time. It can even be mounted without the presence of an X-ray in the operating room. Minor reposition and axial synchronization can be performed without the need for anaesthesia or additional surgery.

Any long bone can be fixed with this technique using only a few components and three rods/tubes, and reliable stabilization of the fracture in terms of axis-length-rotation of the bone is achieved.

The advantages of external fixators are less damage to the blood supply of the bone than with application of an internal nail, minimal interference with the overlying soft tissues, suitability for stabilization of open fractures, adjustability of fixation stiffness without surgery, and a good chance in situations with a risk of infection.

On the contrary, the disadvantages are that pins and wires penetrate soft tissues, patients are restricted in joint movement, complications in pin paths occur with long-term external fixation, they are uncomfortable and not always well tolerated.

For a favourable postoperative condition of the patient, it is most important that the pins are fitted correctly. Post-operative care of the puncture area is also necessary, i.e. cleaning and disinfection, and especially the provision of movement activities in order to avoid muscle weakening and overall weakening of the musculoskeletal system functions (rehabilitation care).

The abovementioned solutions of external fixators are also based on the following patent solutions U2397, U.S. Pat. Nos. 6,840,939B2, 7,147,640B2, 6,537,275B2, US20060129163A1, U.S. Pat. Nos. 10,076,360B2, 5,769,851A, US20130110110A1, U.S. Pat. Nos. 4,570,625A, 7,147,639B2, 9,757,193B2, 4,502,473A and professional scientific articles:

- De Bastiani, G., Aldegheri, R., Renzi B. L. Dynamic axial fixation. International Orthopaedics, 10, pp. 95-99 (1986), from doi: 10.1007/BF00267748;
- Calder, P. R., Faimali, M., Goodier, D. W. The role of external fixation in paediatric limb lengthening and deformity correction. Injury, 50, S18-S23 (2019), from doi: 10.1016/j.injury.2019.03.049;
- Eralp. L., Kocaoglu, M. Distal Tibial Reconstruction with Use of a Circular External Fixator and an Intramedullary Nail. The Journal of Bone & Joint Surgery, 90, pp. 181-194 (2008) from doi: 10.2106/JBJS.H.00467;
- De Bastiani, G., Aldegheri, R., Renzi Brivio, L. The treatment of fractures with a dynamic axial fixator. The Journal of Bone and Joint Surgery. British volume, 66-B (4) (1984) from doi: 10.1302/0301-620X.66B4.6746689;
- Mitkovič/EXTERNAL BONE FIXER FOR APPLICATION IN EXPERIMENTAL SURGERY AND VETERINARY 2020;
- Li Renzeng/Tibia orthopedic external fixation support 2021;
- WANG/Tibia locking nail plate external fixator 2021;
- GonG/Tibia transverse moving external fixation support 2020;
- WEi/Low-incisura locking type external Tibia fixing frame 2020;
- Proximal Tibia External Fixator-Orthopedic Drills &; Medical Devices https://www.orthopedicdrills.com/product/proximal-Tibia-external-fixator/?doing_wp_cron=1663674786.9243218898773193359375.

With conventional solutions, in many cases there is not enough time to apply the fixator.

DISCLOSURE OF INVENTION

The aim of this invention is to provide a safe and quick reposition of a fracture. This aim is achieved by means of an external fixator, described in detail below, which functions on the principle of movable penetration and reposition forceps.

The reposition and penetration forceps for fractures of long bones, in particular traumatic fractures of tibia in centre line, comprise two jaws forming a three-point system in opposition. The first jaw is movable and comprises two threaded pins with tips and the second jaw is firm and comprises one threaded pin with a tip.

The pin tips are conical in shape and their diameter is smaller than the diameter of the pins, thereby they are shaped so as not to penetrate into the medullary cavity. Pin tips can be custom made based on the patient's individual cortical bone thickness.

Pins are interchangeable according to the required length, preferably from 20 to 100 mm, or personalized based on DICOM data regarding the thickness of the compact bone, so as to ensure the possibility of reposition at different localization sites of the fracture.

The jaws of the forceps are advantageously interconnected by a sliding sleeve, which is part of a sliding mechanism for sliding the jaws towards and away from each other. The sliding sleeve can be of different sizes and, as a result, the forceps can be applied in different areas of the limb to be fixed. The forceps work on the principle of a carpenter's clamp.

The sliding mechanism is preferably a spring-lever mechanism comprising a body of the second jaw, the sliding sleeve, a trigger, a handle, a spring and locking inserts. The body of the second jaw is connected to the trigger and the handle used for bringing the jaws closer together by repeatedly pressing the trigger against the handle. The spring serves to return the trigger after being pressed and is blocked on one side by the body of the jaw and on the other side by the locking pins. The inner locking insert is located inside the body of the second jaw between the spring and the locking pins, and the outer locking insert is located outside the body of the second jaw, wherein sliding the outer locking insert towards the body of the jaw releases the forceps.

The spring-lever mechanism inside the second jaw is preferably open with the possibility of separate sterilization and replacement of individual components. The mechanism ensures the locking of the jaw distances and also to a certain extent the stabilization of the jaws relative to each other.

In a preferred embodiment, the trigger and the handle are removable. The significance of their removal is to lighten the fixator during long-term fixation. They can be removed after the locking pins have been removed.

The spring-lever mechanism may comprise a blocking insert for long-term fixation and prevention of unwanted release. The spring-lever mechanism may further comprise a blocking screw for securing the position of the spring.

The reposition forceps can serve independently as an auxiliary tool in the surgery where reposition of fragments is required without the need for external fixation, or they can form part of an external fixator for fractures of long bones.

The external fixator according to this invention is primarily intended for traumatic fractures of tibia in centre line, but it can also be used for treating fractures of other long bones and associated joints. It combines the principle of pinless bone penetration with a modular system of defect stabilization. It can be assigned to pinless, nonmedullary fixators, with the fact that the way of arrangement of the tips, their tightening, repositioning, stabilization and the fixation itself is new.

The external fixator works on the principle of approach forceps, which are composed of two jaws. It comprises at least two sets of forceps described above. The sets of forceps are preferably arranged identically or in a mirror image to each other.

In a preferred embodiment, the sets of forceps are interconnected by a tubular system connected by clamps, which ensures both high variability of movement and stability/firmness of repositioning after securing. The stabilizing tubular system is able to adapt to all positions of application of penetration and reposition forceps related to the nature of the fracture of long bone.

The tubular system comprises threaded rods, at least one connecting rod and locking clamps. Each jaw of each forceps is firmly connected to one threaded rod. Each threaded rod of one set of forceps is connected to the threaded rod of the other set of forceps by at least one connecting rod, preferably by two connecting rods. Each connecting rod is variably adjustable by means of the locking clamps connecting two rods each time.

The entire assembly, which comprises two sets of forceps, contains four threaded rods firmly connected to the forceps and at least two to four connecting rods that are variably adjustable by the number and position and adjustment of the clamps. The dimensions of the rods are chosen based on the location of application and the nature of the fracture. This system can correct the approach/retraction, drop/lift, turning out/in of the forceps relative to each other. It can lock the external fixator in any position.

The connecting rods and the threaded rods preferably have the same diameter. The locking clamps are rotatable in one axis and securable with a butterfly screw. Once secured, they hold the connected rods in a stable position.

Communicating sensors for temperature, applied force, impact and motion, being able of transmitting data in real time to a device for their processing, can be connected to the external fixator.

The components of the external fixator are preferably made of medical metals and/or composites, in particular surgical steel, cobalt chrome, titanium alloy or pure titanium, or eventually of materials based on PAEK, ABS, ASA, NYLON or other plastics and composites with reinforcement, such as carbon or glass fibres. In particular, components of pins, tips, sliding mechanisms, threaded and connecting rods, screws, clamps and nuts can be made of medical metals and/or composites. In particular, handles and bodies of jaws can be made of materials based on PAEK, ABS, ASA, NYLON, or other strength-compliant plastics and composites with reinforcement, e.g. carbon or glass fibres.

The external fixator can be produced by additive manufacturing technology—"ADDITIVE MANUFACTURING", especially using methods such as FDM (Fused Deposition Modeling) from filaments or pellets or SLS (Selective Laser Sintering) or SLM (Selective Laser Melting) from metal or polymer powder, or Binder jetting in combination with chip machining, especially CNC machining and laser machining, or injection of plastics-hybrid production. The advantage of the reposition and penetration forceps and the external fixator according to the present invention is mainly the reduced possibility of spreading inflammation at site of fixation, as there is no penetration of the medullary cavity. Due to the fact that it is not necessary to pre-drill holes for deep penetration, the time of fitting, fixation and correction of a fracture or other deformed bone condition is also reduced. Another benefit over existing fixators is the reduction in weight due to the materials and production technologies used, which is a major problem burdening the patient with all types of existing fixators. Last but not least, this new type of external fixator significantly increases the stability of fracture fixation compared to the existing so-called pinless fixators that do not penetrate into the medullary cavity. Thanks to the quick fitting possibility, the reposition forceps can ensure safe and quick reposition of a fracture, especially in severe polytraumas, in which it is necessary to focus mainly on the restoration of vital functions and fractures are dealt with secondarily.

EXAMPLES

Example 1

Figure 1:
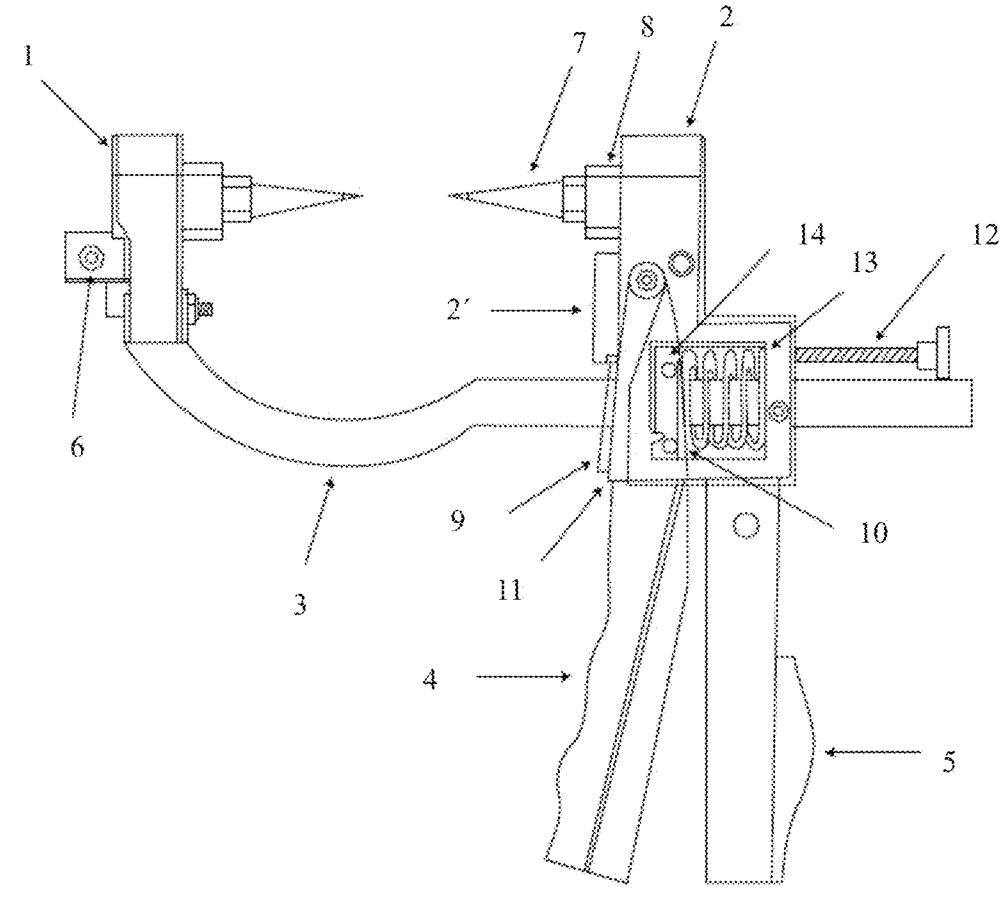
FIG. 1 shows the set of reposition and penetration forceps and the mechanism of moving and locking the jaws in 2D view.
Figure 2:
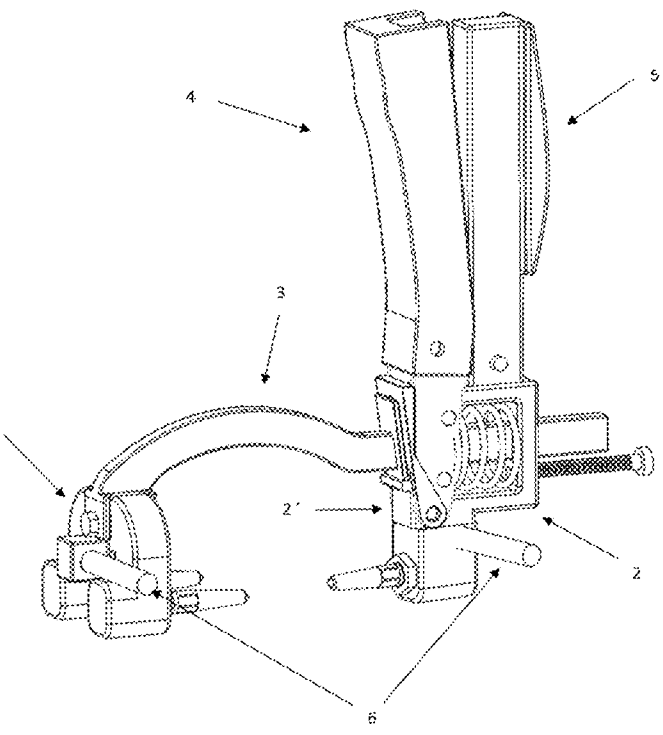
FIG. 2 shows the set of reposition and penetration forceps in 3D view.
Figure 3:
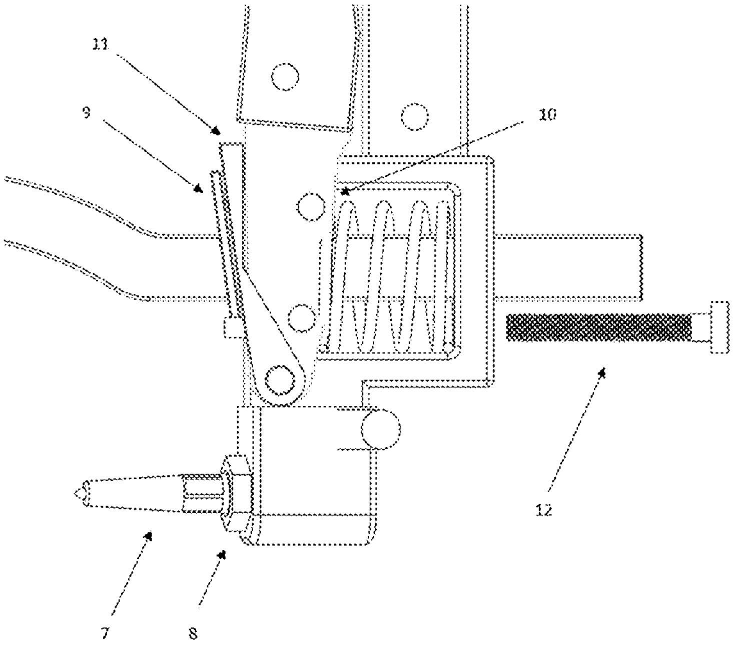
FIG. 3 shows a detail of the second jaw body and part of the spring-lever mechanism.
Figure 4:
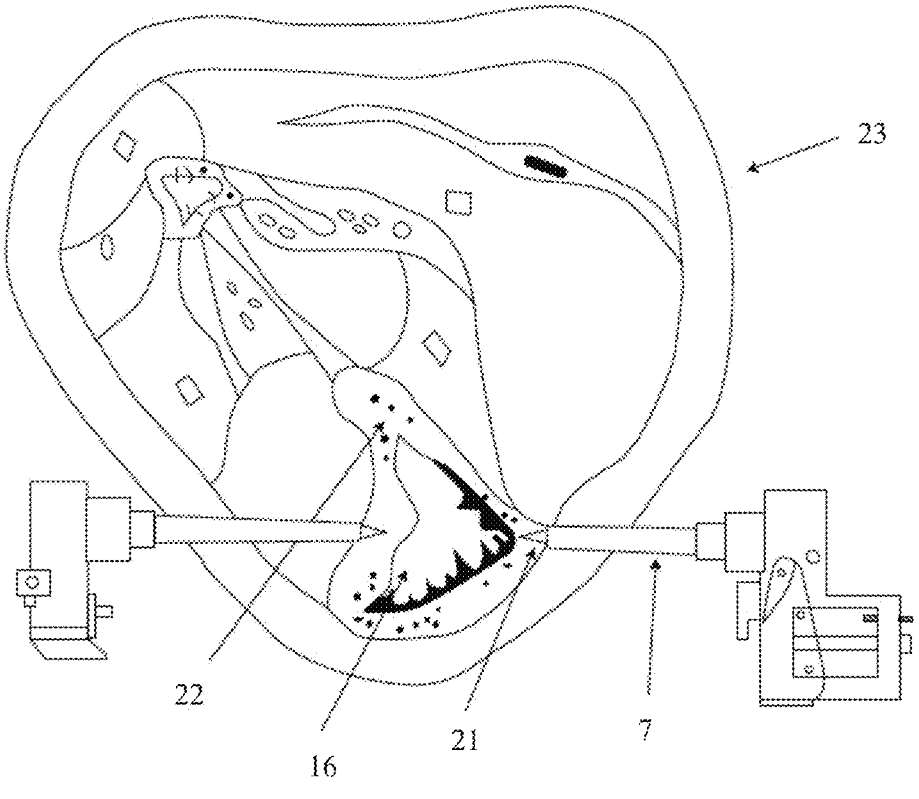
FIG. 4 shows the penetration of the pin tips of the forceps into the bone compacta without interference of the medullary canal.
Figure 5:
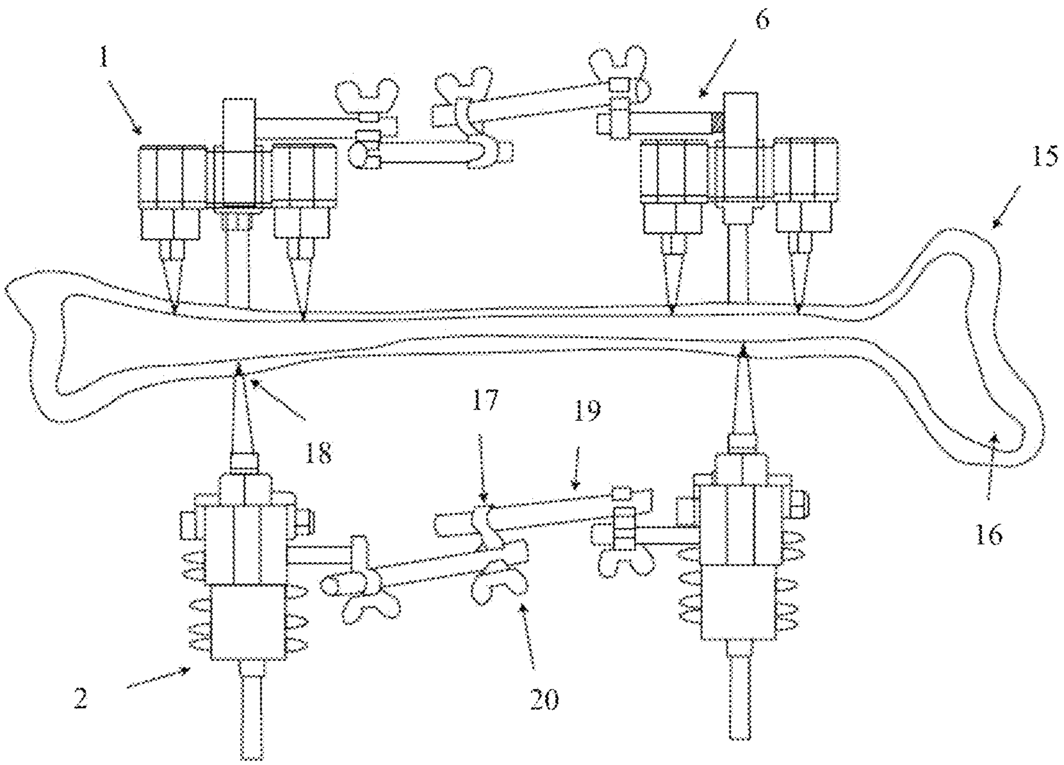
FIG. 5 shows the entire assembly of the external fixator in 2D view and its location on the tibia.
Figure 6:
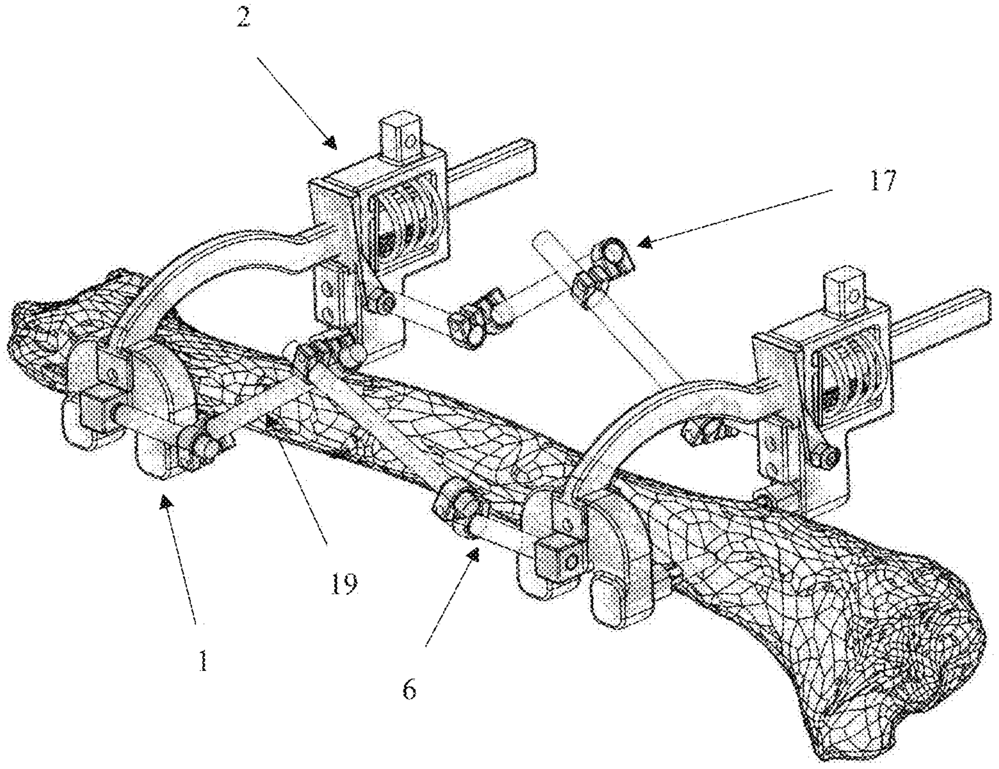
FIG. 6 shows the entire assembly of the external fixator in 3D view and its location on the tibia.

The reposition and penetration forceps for fractures of long bones according to the FIG. 1. were made. The forceps comprise two jaws forming a three-point system in opposition. The first movable jaw 1 comprises two threaded pins 7 with tips 21 and the second firm jaw 2 comprises one threaded pin 7 with a tip 21.

The tips 21 of the pins 7 are conical in shape and their diameter is smaller than the diameter of the pin 7, thereby they are shaped so as not to penetrate into the medullary cavity. The pins 7 are interchangeable according to the required length, from 20 to 100 mm.

The first jaw 1 and the second jaw 2 are interconnected by the sliding sleeve 3 which is part of the sliding mechanism for sliding the jaws 1,2 towards and away from each other.

The sliding mechanism is a spring-lever mechanism comprising the body of the second jaw 2, the sliding sleeve 3, the trigger 4, the handle 5, the spring 13 and the locking inserts 9,10. The body of the second jaw 2 is connected to the trigger 4 and the handle 5 used for bringing the jaws 1,2 closer together by repeatedly pressing the trigger 4 against the handle 5. The spring 13 serves to return the trigger 4 after being pressed and it is blocked on one side by the body of the jaw 2 and on the other side by the locking pins 14. The inner locking insert 10 is located inside the body of the second jaw 2 between the spring 13 and the locking pins 14. The outer locking insert 9 is located outside the body of the second jaw 2. By sliding the outer locking insert 9 towards the body of the jaw 2, the forceps are released.

The trigger 4 and the handle 5 are removable. The spring-lever mechanism further comprises the blocking insert 11 for long-term fixation and prevention of unwanted release and the blocking screw 12 for securing the position of the spring 13.

Example 2

The reposition and penetration forceps were made, wherein the spring-lever approach system is located on the body of the firm second jaw 2, which moves the sliding sleeve 3 on which the movable first jaw 1 is located. The movement is provided by a spring system with two locking inserts-one inner insert 10 inside the body of the second jaw 2, inserted between the spring 13 and the locking pins 14, and one outer insert 9 outside the body of the second jaw 2, inserted in a cut-out of the handle 2' of the locking insert with precise apertures for the entry of the sliding sleeve 3.

By repeatedly pressing the lever mechanism, the jaws are brought closer to each other step by step. The pins 7 are personalized so as to ensure the possibility of reposition at different localization sites of the fracture. The pin tips 21 were applied to the safe zones of the long bones. For the safety of the patient, the system works on the principle of a torque wrench with a jump force value set according to the limit values of compact bone destruction.

Example 3

The external fixator for fractures of long bones was made, comprising two sets of forceps according to Example 1. The sets of forceps are arranged in a mirror image.

The sets of forceps are interconnected by the tubular system comprising two threaded rods 6, two connecting rods 19 and six locking clamps 17. Each jaw 1,2 of each forceps is firmly connected to one threaded rod 6 and each threaded rod 6 of set of forceps is connected to the threaded rod 6 of the other set of forceps by two connecting rods 19. Each connecting rod 19 is variably adjustable by means of the locking clamps 17 connecting two rods each time.

The connecting rods 19 and the threaded rods 6 have the same diameter, which allows them to be connected by means of the clamps. The locking clamps 17 are rotatable in one axis and are securable with the butterfly screw 20.

The components of the fixator are made of medical metals and/or composites and of PAEK-based materials. The external fixator was manufactured by additive manufacturing technology, namely by the FDM (Fused Deposition Modeling) method.

Example 4

The external fixator for fractures of long bones was made, comprising two sets of forceps arranged identically to each other. The tubular stabilization system was connected to a pair of reposition forceps with the tips 21 applied in the safe zones of the long bones by means of the threaded rods 6 which are threadedly connected to the bodies of the jaws 1,2. The system is connected by the locking clamps 17, which use butterfly screws 20 to lock the system. In addition to the threaded rods 6, the tubular stabilization system comprises one connecting rod 19 which connects the jaws of the different sets of forceps. Four locking clamps 17 were used for the entire assembly.

Example 5

The external fixator for fractures of long bones was made, comprising three sets of forceps. Such fixator is suitable for use in rare complex cases. The tubular stabilization system was modified as required.

Example 6

A SMART solution for a fixation system was made. The communicating sensors for temperature, applied force, impact and motion, which send data in real time to a device that can process it, were connected to Examples 3, 4 and 5. Using a software application in a mobile device, the external fixator is monitored and alerts the patient or clinical staff of any loosening of the fixator or inflammatory processes.

INDUSTRIAL APPLICABILITY

The reposition and penetration forceps and the external fixator for fractures of long bones are primarily intended for application in traumatology and orthopaedics, with the possibility of use in other related fields as well.

LIST OF REFERENCE NUMERALS

1 First jaw
2 Second jaw
2' Locking insert handle
3 Sliding sleeve
4 Trigger
5 Handle
6 Threaded rod
7 Pin
8 Threaded insert for pin
9 Outer locking insert
10 Inner locking insert
11 Blocking insert
12 Blocking screw
13 Spring
14 Locking pin
15 Tibia
16 Medullary cavity of tibia
17 Locking clamp
18 Pin stop on Corticalis
19 Connecting rod
20 Butterfly screw
21 Pin tip
22 Corticalis
23 Lower limb cross-section

The invention claimed is:

1. Reposition and penetration forceps for fractures of long bones, characterized in that the forceps comprise two jaws forming a three-point system in opposition, wherein a first movable jaw (1) comprises two threaded pins (7) with pin tips (21) and a second firm jaw (2) comprises one threaded pin (7) with a tip (21), and wherein a sliding mechanism for sliding the jaws (1,2) towards and away from each other is a spring-lever mechanism comprising a body of the second firm jaw (2), a sliding sleeve (3), a trigger (4), a handle (5), a spring (13), an outer locking insert (9), and an inner locking insert (10), wherein:

(a) the body of the second firm jaw (2) is connected to the trigger (4) and the handle (5) used for bringing the first movable jaw (1) and the second firm jaw (2) closer together by pressing the trigger (4) against the handle (5), (b) the spring (13) for returning the trigger (4) after being pressed is blocked on one side by the body of the second firm jaw (2) and on the other side by locking pins (14), (c) the inner locking insert (10) is located inside the body of the second firm jaw (2) between the spring (13) and the locking pins (14) and the outer locking insert (9) is located outside the body of the second firm jaw (2), wherein sliding the outer locking insert (9) towards the body of the second firm jaw (2) releases the forceps.

2. The reposition and penetration forceps according to claim 1, characterized in that the pin tips (21) are conical in shape and their diameter is smaller than the diameter of the pins (7), thereby they are shaped so as not to penetrate into the medullary cavity.

3. The reposition and penetration forceps according to claim 1, characterized in that the pins (7) are interchangeable according to a required length, from 20 to 100 mm, or personalized so as to ensure the possibility of reposition at different localization sites of the fracture.

4. The reposition and penetration forceps according to claim 1, characterized in that the first movable jaw (1) and the second firm jaw (2) are interconnected by the sliding sleeve (3) which is part of the sliding mechanism.

5. The reposition and penetration forceps according to claim 1, characterized in that the trigger (4) and the handle (5) are removable.

6. The reposition and penetration forceps according to claim 1, characterized in that the spring-lever mechanism comprises a blocking insert (11) for long-term fixation and prevention of unwanted release.

7. The reposition and penetration forceps according to claim 1, characterized in that the spring-lever mechanism comprises a blocking screw (12) for securing the position of the spring (13).

8. The reposition and penetration forceps according to claim 1, characterized in that the forceps form part of an external fixator for fractures of long bones.

9. An external fixator for fractures of long bones, characterized in that the external fixator comprises at least two sets of forceps according to claim 1, wherein the sets of forceps are arranged identically or in a mirror image to each other.

10. The external fixator according to claim 9, characterized in that the sets of forceps are interconnected by a tubular system comprising threaded rods (6), at least one connecting rod (19) and locking clamps (17), in such manner that the first movable jaw (1) and the second firm jaw (2) of each forceps is firmly connected to one threaded rod (6) and each threaded rod (6) of one set of forceps is connected to the threaded rod (6) of the other set of forceps by at least one connecting rod (19), wherein each connecting rod (19) is variably adjustable by means of the locking clamps (17) connecting two rods each time.

11. The external fixator according to claim 10, characterized in that the connecting rods (19) and the threaded rods (6) have the same diameter and/or the locking clamps (17) are rotatable in one axis and are securable with a butterfly screw (20).

12. The external fixator according to claim 9, characterized in that communicating sensors for temperature, applied force, impact and motion can be connected thereto, being able of transmitting data in real time to a device for their processing.

13. The external fixator according to claim 9, characterized in that the components thereof are made of medical metals and/or composites, and/or materials based on PAEK, ABS, ASA, NYLON or other plastics and composites with reinforcement.

14. The external fixator according to claim 9, characterized in that the external fixator is produced by additive manufacturing technology.

* * * * *